(12) United States Patent
Sugawara

(10) Patent No.: US 10,650,926 B2
(45) Date of Patent: May 12, 2020

(54) PUMP MONITORING SYSTEM AND PUMP MONITORING SERVER

(71) Applicant: TERUMO KABUSHIKI KAISHA, Tokyo (JP)

(72) Inventor: Hideki Sugawara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 157 days.

(21) Appl. No.: 15/714,426

(22) Filed: Sep. 25, 2017

(65) Prior Publication Data
US 2018/0018440 A1    Jan. 18, 2018

Related U.S. Application Data

(63) Continuation of application No. PCT/JP2016/052233, filed on Jan. 27, 2016.

(30) Foreign Application Priority Data

Mar. 26, 2015 (JP) .................. 2015-064045

(51) Int. Cl.
| | |
|---|---|
| G16H 40/63 | (2018.01) |
| A61M 5/142 | (2006.01) |
| G16H 20/17 | (2018.01) |
| G16H 40/67 | (2018.01) |
| A61M 5/172 | (2006.01) |
| G06F 19/00 | (2018.01) |

(52) U.S. Cl.
CPC ............ G16H 40/63 (2018.01); A61M 5/142 (2013.01); A61M 5/172 (2013.01);
(Continued)

(58) Field of Classification Search
CPC ........ G16H 40/63; G16H 20/17; G16H 40/67; A61M 5/172; A61M 5/142;
(Continued)

(56) References Cited

U.S. PATENT DOCUMENTS

| 8,560,345 B2 * | 10/2013 | Wehba ................. A61M 5/142 705/3 |
| 2007/0233521 A1 * | 10/2007 | Wehba ................. A61M 5/142 705/3 |

(Continued)

FOREIGN PATENT DOCUMENTS

| JP | 2008-516303 | 5/2008 |
| JP | 2009-531146 A | 9/2009 |

(Continued)

OTHER PUBLICATIONS

International Search Report (with English translation) and Written Opinion for International (PCT) Patent Application No. PCT/JP2016/052233, dated Mar. 22, 2016, 8 pages.

(Continued)

*Primary Examiner* — Ziaul Karim
(74) *Attorney, Agent, or Firm* — Jason H. Vick; Sheridan Ross, PC

(57) ABSTRACT

A server control unit of a pump monitoring server records, in a recording unit, a state of a pump together with a time at which the state of the pump is confirmed in a case where the server control unit has received the state of the pump confirmed by a medical practitioner from the pump within a first predetermined time from the start of clocking of a liquid delivery time by a clocking unit. In contrast, in a case where the server control unit has not received the state of the pump from the pump even after the first predetermined time has elapsed from the start of the clocking of the liquid delivery time by the clocking unit, the server control unit prompts the medical practitioner to confirm the pump.

20 Claims, 6 Drawing Sheets

(52) U.S. Cl.
   CPC ......... *G06F 19/3468* (2013.01); *G16H 20/17* (2018.01); *G16H 40/67* (2018.01); *A61M 2205/18* (2013.01); *A61M 2205/3561* (2013.01); *A61M 2205/50* (2013.01); *A61M 2205/502* (2013.01); *A61M 2205/52* (2013.01)

(58) Field of Classification Search
   CPC ...... A61M 2205/3561; A61M 2205/18; A61M 2205/52; A61M 2205/50; A61M 2205/502; G06F 19/3468
   USPC .......................................................... 700/283
   See application file for complete search history.

(56) References Cited

U.S. PATENT DOCUMENTS

| | | | |
|---|---|---|---|
| 2013/0281965 A1* | 10/2013 | Kamen | A61M 5/172 604/500 |
| 2013/0317753 A1 | 11/2013 | Kamen et al. | |
| 2014/0188076 A1* | 7/2014 | Kamen | A61M 5/1408 604/506 |

FOREIGN PATENT DOCUMENTS

| | | |
|---|---|---|
| JP | 2012-110586 A | 6/2012 |
| JP | 2013-153945 | 8/2013 |
| JP | 2014-006915 | 1/2014 |
| WO | WO 2007/126948 | 11/2007 |
| WO | WO 2009/023634 | 2/2009 |

OTHER PUBLICATIONS

International Preliminary Report on Patentability for International (PCT) Patent Application No. PCT/JP2016/052233, dated Oct. 5, 2017.

Notice of Reasons for Refusal (Including Translation) for corresponding Japanese Patent Application No. 2017-507546, dated Sep. 10, 2019.

* cited by examiner

FIG. 6

PUMP MONITORING SYSTEM AND PUMP MONITORING SERVER

CROSS REFERENCE TO RELATED APPLICATIONS

The present application is a continuation of and claims priority to and the benefit of, under 35 U.S.C. § 119(e), PCT Application No. PCT/JP2016-052233, filed on Jan. 27, 2016, which claims priority to Japanese Patent Application No. 2015-064045, filed Mar. 26, 2015, entitled "PUMP MONITORING SYSTEM AND PUMP MONITORING SERVER," the entire disclosures of each of these applications is incorporated herein by reference in their entirety, for all that they teach and for all purposes.

TECHNICAL FIELD

The present invention relates to a pump monitoring system and a pump monitoring server for monitoring a state of a pump, for example.

BACKGROUND

In a medical field such as a hospital, medical pumps such as infusion pumps and syringe pumps are used as pumps for administering medicines into the body of a patient. Generally, these medical pumps are used to deliver one type of medicine. For this reason, in a case where a plurality of types of medicines is simultaneously administered to a patient in an operating room, an intensive care room, or the like, several medical pumps, in a number according to the types of medicine, are needed.

Even in a case where a plurality of pumps is used for one patient, it is possible to allow each of the pumps to deliver a plurality of types of medicine at different timings, flow rates, or the like. A medical practitioner (for example, a nurse) monitors the states of the pump (name of the medicine delivered by the pump, flow rate, amount of delivered medicine, or the like) so as to prevent the flow rate of the medicine delivered by the pump from exceeding a predetermined range, or prevent shortage of the medicine. Unfortunately, however, it is difficult for a medical practitioner to oversee each of the pumps and constantly confirm the state of the pump.

Japanese Patent Application No. JP 2014-6915 A discloses an arrangement in which a server stores a medical device maintenance schedule including a reminder for executing maintenance on a medical device in a computing system isolated from the medical device and transmits the reminder from the computing system to the medical device.

SUMMARY

Conventionally, a medical practitioner periodically patrols a hospital room to confirm the state of the pump while a pump is delivering a liquid. The state of the pump confirmed by the medical practitioner is recorded by marking with a pen on a syringe or infusion bag, personal memo writing, or the like, in many cases. This recordation at the pump makes it difficult to share a result of confirming the pump with other medical practitioners, and thus, medical practitioners have difficulty in grasping the time at which other medical practitioners confirmed the pump. In another case where the monitoring intervals of the pumps are managed for each of the medical practitioners, confirmation of the pump might be delayed.

The technique disclosed in Japanese Patent Application No. JP 2014-6915 merely transmits a reminder to a user of the pump when a maintenance event occurs in accordance with a maintenance schedule. This reminder leads to a difficulty in grasping by the computing system, disclosed in Japanese Patent Application No. JP 2014-6915, whether the pump has been confirmed, making it still difficult to achieve uniform management of the state of the pump.

The embodiments presented herein have been made in view of this situation, and an object thereof is to achieve efficient confirmation of the state of the pump.

A pump monitoring system, according to the embodiments presented herein, includes a pump configured to deliver a medicine to a patient and a pump monitoring server configured to monitor the state of the pump.

The pump includes a pump control unit for transmitting the state of the pump confirmed by the medical practitioner to the pump monitoring server.

The pump monitoring server includes a clocking unit configured to clock the liquid delivery time of the pump, and a server control unit. In a case where the server control unit received the state of the pump from the pump within a first predetermined time from the start of clocking of the liquid delivery time by the clocking unit, the server control unit records in the recording unit the state of the pump together with the time at which the state of the pump is confirmed. In contrast, in a case where the server control unit has not received the state of the pump from the pump even after the first predetermined time has elapsed from the start of the clocking of the liquid delivery time by the clocking unit, the server control unit prompts the medical practitioner to confirm the pump.

According to the embodiments presented herein, the state of the pump confirmed by the medical practitioner is uniformly managed by the pump monitoring server. In a case where the state of the pump has not been confirmed within a predetermined time, the pump monitoring server prompts the medical practitioner to confirm the pump, making it possible to efficiently manage the state of the pump.

The problems, configurations, and effects other than those described above will be specified by the following description of embodiments.

BRIEF DESCRIPTION OF DRAWINGS

FIG. 6 is a screen configuration diagram illustrating an exemplary display of an individual monitoring screen according to the embodiments presented herein.

DETAILED DESCRIPTION

Figure 1:
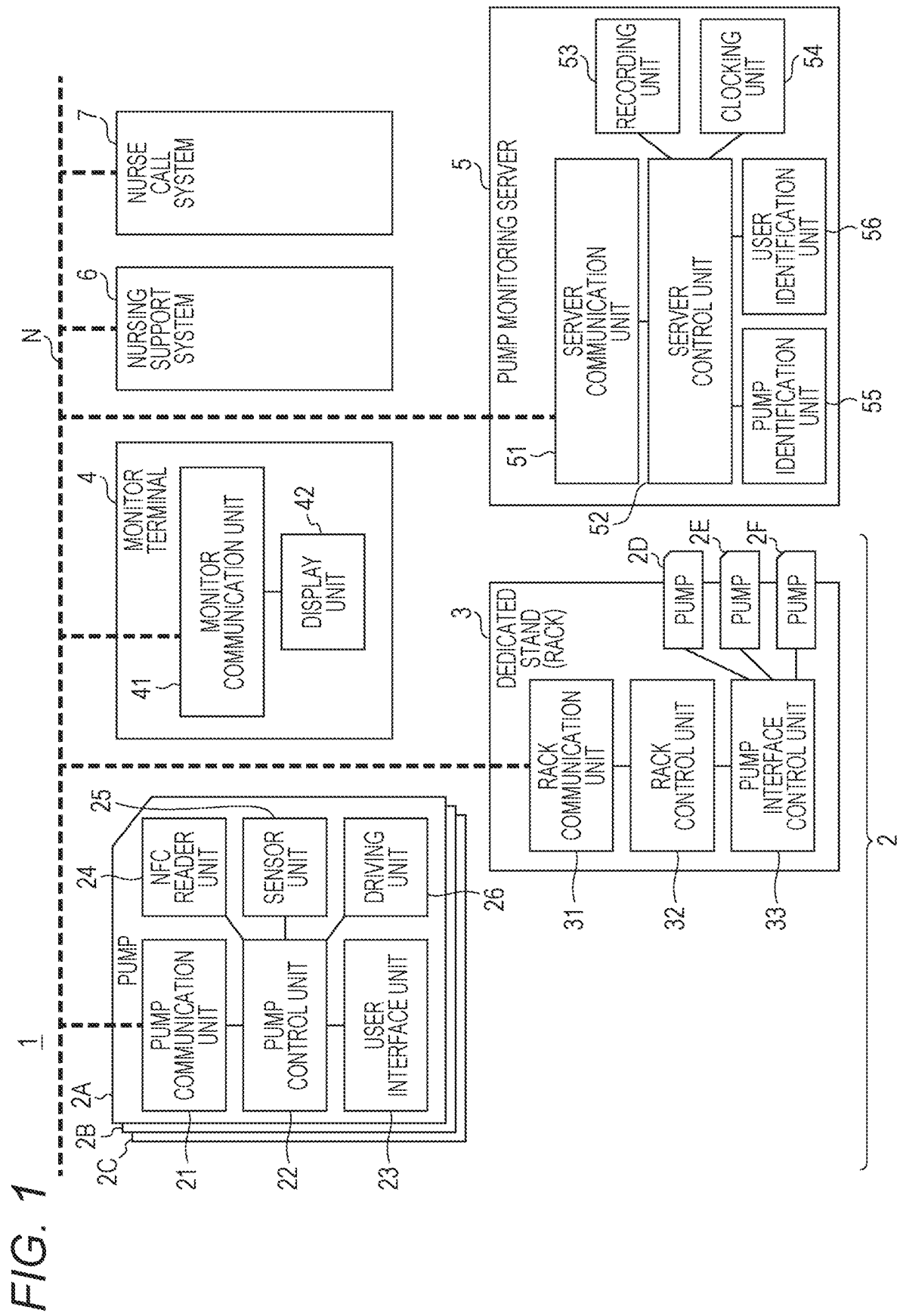
FIG. 1 is a block diagram illustrating an overall configuration example of a pump monitoring system according to the embodiments presented herein.

Hereinafter, a pump monitoring system and a pump monitoring server according to the embodiments presented herein will be described with reference to FIGS. 1 to 3. In this specification and the drawings, components having substantially the same function or configuration are denoted by the same reference numerals, and redundant explanations are omitted.

FIG. 1 is a block diagram illustrating an overall configuration example of a pump monitoring system 1.

The pump monitoring system 1 includes medical pumps 2A to 2C mutually connected to an in-hospital network N, a dedicated stand 3 (also referred to as "rack") to which medical pumps 2D to 2F are attached, a monitor terminal 4, a pump monitoring server 5, a nursing support system 6, and a nurse call system 7.

The pumps 2A to 2C are independently connected to an in-hospital network N and the pumps 2D to 2F are connected to the in-hospital network via a dedicated stand 3. The in-hospital network N is configured with a wireless or wired local area network (LAN). The monitor terminal 4, the pump monitoring server 5, the nursing support system 6, and the nurse call system 7 are connected to the in-hospital network N configured with a wired LAN.

The pump 2A includes a pump communication unit 21, a pump control unit 22, a user interface unit 23, a near field communication (NFC) reader unit 24, a sensor unit 25, and a driving unit 26, and delivers a medicine to a patient. In the following description, a configuration example and an operation example of the pump 2A will be described, and a detailed description of the pumps 2B to 2F having a configuration similar to the configuration of the pump 2A will be omitted. Moreover, in a case where there is no need to distinguish between the pumps 2A to 2F, they will be collectively referred to as the "pump 2".

The pump communication unit 21 is used as a communication interface configured to convert data transmitted to the in-hospital network N by the pump control unit 22 or convert data received from the in-hospital network N. Communication performed by the pump communication unit 21 is started every several minutes or at a timing when the pump control unit 22 transmits and receives various types of data to and from the pump monitoring server 5. Moreover, the pump communication unit 21 can perform infrared communication with a pump interface control unit 33 of the dedicated stand 3.

The pump control unit 22 includes a ROM and RAM, and performs processing, judgment, and control of the operation of each of portions in the pump 2A. The pump control unit 22 transmits the state of the pump 2A and user identification information of the medical practitioner who confirmed the pump 2A to the pump monitoring server 5 via the pump communication unit 21. Note that the state of the pump 2A includes the liquid delivery state of the pump 2A (distinction between delivering or stopping), the name of the medicine to be delivered, the flow rate, the administered amount (integrated amount), scheduled administration amount, and remaining medicine amount.

The user interface unit 23 is, for example, a touch panel attached to a side surface of the pump 2. The medical practitioner, or the like, can set the operation of the pump 2A by performing operation input into the user interface unit 23. The user interface unit 23 displays a current operation situation of the pump 2A, the remaining medicine amount, or the like. The user interface unit 23 is provided on a casing of the pump 2A and serves as a confirmation button for inputting a fact that the medical practitioner has confirmed the state of the pump 2. When the medical practitioner presses the confirmation button after confirming the pump 2A, confirmation information is transmitted to the pump monitoring server 5 by the pump control unit 22. Thereafter, the pump control unit 22 transmits the state of the pump 2A to the pump monitoring server 5.

The NFC reader unit 24 is an exemplary reading unit that performs proximity wireless communication with an NFC tag (an exemplary storage medium) built in a name tag or a portable terminal (for example, personal handy-phone system (PHS) and smartphone) possessed by a medical practitioner, or the like, and that reads the user identification information of the medical practitioner from the NFC tag. The user identification information read by the NFC reader unit 24 is transmitted to the pump control unit 22. The pump control unit 22 transmits the user identification information read by the NFC reader unit 24 from the NFC tag together with the reading time to the pump monitoring server 5 via the in-hospital network N.

The sensor unit 25 detects whether an infusion tube connected to an infusion bag containing a medicine or a syringe containing a medicine is attached at a predetermined position of the pump 2A. Information that the sensor unit 25 detects that the infusion tube or syringe is attached to the pump 2A is transmitted to the pump control unit 22. The pump control unit 22 manages the time at which the infusion tube or syringe is attached to the pump 2A.

When the pump 2A is an infusion pump, for example, the driving unit 26 delivers the medicine in the tube by sequentially pressing the infusion tube (so-called peristaltic type) with a plurality of fingers for liquid delivery. In a case where the pump 2A is a syringe pump, a syringe presser is pressed. The pump control unit 22 can calculate the amount of medicine delivered from the infusion pump or the syringe by the driving unit 26 on the basis of a moving distance of the driving unit 26, or the like.

Next, a configuration example and an operation example of the dedicated stand 3 will be described.

The dedicated stand 3 includes a rack communication unit 31, a rack control unit 32, and the pump interface control unit 33. Pumps 2D to 2F are attached on the dedicated stand 3.

The rack communication unit 31 is used as a communication interface configured to convert data transmitted by the rack control unit 32 to the in-hospital network N or convert data received from the in-hospital network N.

The rack control unit 32 includes a ROM and a RAM, and performs processing, judgment and control of the operation of each of portions in the dedicated stand 3. Together with this, the rack control unit 32 grasps the operation situation of the pumps 2D to 2F attached on the dedicated stand 3. Subsequently, the rack control unit 32 transmits from the pumps 2D to 2F, the states of the pumps 2D to 2F and the user identification information of the medical practitioner who has confirmed the pumps 2D to 2F to the pump monitoring server 5.

Pumps 2D to 2F are connected to the pump interface control unit 33. When the pumps 2D to 2F are attached to the dedicated stand 3, the pump communication unit 21 of the pumps 2D to 2F and the pump interface control unit 33 of the dedicated stand 3 perform wireless connection with each other by infrared communication. Thereafter, the pump interface control unit 33 judges whether the pumps 2D to 2F have been properly attached to the dedicated stand 3. Subsequently, in a case where the pump interface control unit 33 judges that the pumps 2D to 2F are attached to the dedicated stand 3, the pump interface control unit 33 performs control including transmission of various data received from the pumps 2D to 2F attached to the dedicated stand 3 to the rack control unit 32 and transmission of control instructions received from the rack control unit 32 to the pumps 2D to 2F.

Next, a configuration example and an operation example of the monitor terminal 4 will be described.

The monitor terminal 4 includes a monitor communication unit 41 and a display unit 42 and is used as an exemplary display terminal. The monitor terminal 4 is installed in an area where the medical practitioners gather, such as a nurse station, and displays a layout of a hospital room to accommodate a patient and the state of the pump 2 installed in the hospital room. With this arrangement, the medical practitioner can monitor the state of the pump 2 via the monitor terminal 4.

The monitor communication unit 41 is connected to the in-hospital network N and transmits the data received from the in-hospital network N to the display unit 42.

The display unit 42 displays the data received from the monitor communication unit 41. For example, the display unit 42 is formed with a liquid crystal display and displays a central monitoring screen (refer to FIG. 3 to be described below).

Next, a configuration example and operation example of the pump monitoring server 5 will be described.

The pump monitoring server 5 includes a server communication unit 51, a server control unit 52, a recording unit 53, a clocking unit 54, a pump identification unit 55, and a user identification unit 56 and can monitor the state of the pump 2.

The server communication unit 51 is used as a communication interface configured to convert data transmitted by the server control unit 52 to the in-hospital network N or convert data received from the in-hospital network N.

The server control unit 52 can include a memory (e.g., ROM and/or a RAM), and performs processing, judgment, and control of the operation of each of portions in the pump monitoring server 5. Moreover, the server control unit 52 receives from the pump 2 various types of information indicating the state of the pump 2. On the basis of the pump identification information received from the pump identification unit 55 and the user identification information received from the user identification unit 56, the server control unit 52 records, in the recording unit 53, information indicating when and by whom the pump 2 was confirmed and together with this information, transmits a confirmation result to the nursing support system 6. Moreover, on the basis of a difference between the time of the timer received from the clocking unit 54 and the reading time of the NFC reader unit 24 received from the pump 2, the server control unit 52 can generate and/or send to the pump 2 and monitor terminal 4 an alarm message instructing the medical practitioner to confirm the pump 2. A specific example of the processing of the server control unit 52 may be as described below with reference to FIG. 2.

The recording unit 53 records the confirmation result, such as the pump identification information, of the pump 2 confirmed by the medical practitioner, the user identification information of the medical practitioner, the reading time of the NFC reader unit 24 as a confirmation history of the pump 2. As the recording unit 53, for example, a large capacity recording medium such as a hard disk drive (HDD) may be used.

When the pump 2 starts delivering the medicine, the clocking unit 54 automatically starts clocking on the timer (liquid delivery time) for each of the pumps 2 under the control of the server control unit 52. A first predetermined time can arbitrarily be set, changed and input by a qualified person in accordance with the working shift of nurses, or the like, in individual hospital wards and hospital rooms in about 5 to 10 minutes, for example. The clocking unit 54 clocks for each of the pumps 2 the time that has elapsed from the time at which the medical practitioner last confirmed the pump 2. The server control unit 52 receives the state of the pump 2 from the pump 2, and then, the clocking unit 54 cancels (resets) the timer and thereafter resumes clocking with the timer under the control of the server control unit 52.

The pump identification unit 55 holds pump identification information uniquely assigned to each of the pumps 2 to identify the pump 2. The pump identification unit 55 transmits the pump identification information indicating who is using the pump 2 confirmed by the medical practitioner in which hospital room, to the server control unit 52.

The user identification unit 56 holds the user identification information of the medical practitioner and transmits the user identification information of the medical practitioner who confirmed the pump 2 to the server control unit 52.

The nursing support system 6 can record, in a recording unit (not illustrated), the time of confirmation of the pump 2 performed by the medical practitioner, the liquid delivery amount of the pump 2, or the like, received from the pump monitoring server 5, and can indicate the recorded content to another medical practitioner. Moreover, by operating a personal computer (PC) or the like (not illustrated) connected to the nursing support system 6, the medical practitioner can also input patient real-time biological information, for example, the time of measuring the body temperature, and the body temperature, as a time-stamp.

The nurse call system 7 alarms to the medical practitioner in a case where the confirmation of the pump 2 is not performed as scheduled, in a case where an abnormality occurs in the pump 2, or the like. In addition, the nurse call system 7 records and manages the affiliation, or the like, of the medical practitioner in a recording unit (not illustrated). In a case where the confirmation of the prompted medical practitioner has not been performed after the predetermined time elapses, it is also possible to issue an alarm to a member, or the like, in the team to which the medical practitioner belongs.

For example, a central processing unit (CPU) can be used as the pump control unit 22, the rack control unit 32, and the server control unit 52. Moreover, for example, a network interface card (NIC), or the like, can be used as the pump communication unit 21, the rack communication unit 31, the monitor communication unit 41, and the server communication unit 51.

<Exemplary Processing of Pump Monitoring System>

Figure 2:
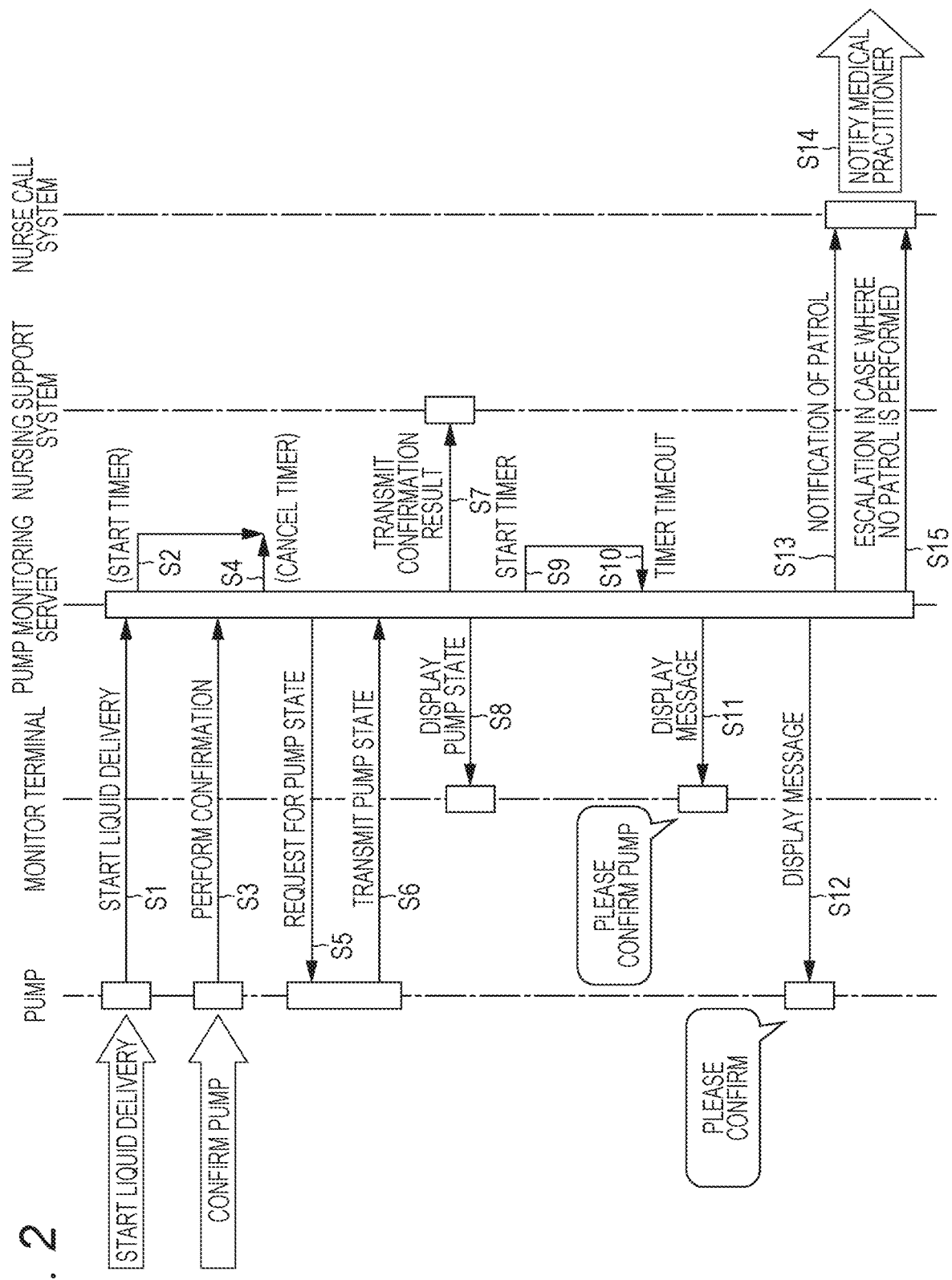
FIG. 2 is a sequence diagram illustrating exemplary processing of each of portions of the pump monitoring system according to the embodiments presented herein.

FIG. 2 is a sequence diagram illustrating an exemplary processing of each of portions of the pump monitoring system 1. In FIG. 2, the pump control unit 22 is substituted with the pump 2, and the server control unit 52 is substituted with the pump monitoring server 5.

First, processing at normal times will be described.

When the pump 2 has started delivering the medicine, the pump 2 notifies the pump monitoring server 5 of the liquid delivery start of the pump 2 (S1). Upon notification of the start of liquid delivery from the pump 2, the pump monitoring server 5 causes the clocking unit 54 to start clocking with a timer (S2). Subsequently, the pump monitoring server 5 monitors the timer clocked by the clocking unit 54.

When the medical practitioner confirms the operation of the pump 2 and presses the confirmation button, the user identification information, the reading time of the user identification information by the NFC reader unit 24, and the confirmation information of the pump 2 are transmitted from the pump 2 to the pump monitoring server 5 (S3). In a case where the pump monitoring server 5 receives the confirmation information within a first predetermined time (for example, two hours) from the start of the clocking with the timer by the clocking unit 54, the pump monitoring server 5 cancels (resets) the timer by the clocking unit 54 (S4). Thereafter, the pump monitoring server 5 causes the clocking unit 54 to resume clocking with the timer.

Next, the pump monitoring server 5 requests the pump 2 to transmit the state of the pump 2 (S5). Upon receiving this request, the pump 2 transmits the state of the pump 2 to the pump monitoring server 5 (S6).

Upon receiving the state of the pump 2, the pump monitoring server 5 records the state of the pump 2 in the recording unit 53, together with the time at which the state of the pump 2 is confirmed (that is, the time of reading the user identification information). Then, the pump monitoring server 5 confirms whether the state of the pump 2 is normal or abnormal.

Thereafter, the pump monitoring server 5 transmits to the nursing support system 6 a confirmation result of the state of the pump 2, for example, the time at which the state of the pump 2 is confirmed, the administered amount (integrated amount) of the medicine (S7) and allows the state of the pump 2 to be displayed on the monitor terminal 4 (S8). The nursing support system 6 performs predetermined processing in accordance with the confirmation result. The processing of steps S2 to S8 is repeated while the pump 2 is delivering the liquid.

Next, processing at the occurrence of timeout of the timer will be described.

As described above, when the medical practitioner has confirmed the operation of the pump 2, the pump monitoring server 5 cancels the timer, and thereafter, the clocking unit 54 resumes clocking with the timer (S9). Thereafter, in a case where confirmation of the pump 2 by the medical practitioner is not performed even after the timer passed the above-described first predetermined time, the pump monitoring server 5 cannot receive the confirmation information from the pump 2 and thus judges that the timeout of the timer occurred (S10).

At this time, the pump monitoring server 5 allows an alarm message to be displayed on the monitor terminal 4 (S11) and prompts the medical practitioner to confirm the pump 2. An exemplary alarm message displayed on the monitor terminal 4 is "Please confirm the pump." The pump monitoring server 5 also allows an alarm message to be displayed on the user interface unit 23 of the pump 2 (S12). An exemplary alarm message displayed on the user interface unit 23 is "Please confirm."

Furthermore, after prompting the medical practitioner to confirm the pump 2, the pump monitoring server 5 sends a patrol prompting notification to the nurse call system 7 (S13). The nurse call system 7 transmits a message prompting monitoring of the pump 2 to a portable terminal possessed by the medical practitioner (S14).

In a case where confirmation of the pump 2 by the medical practitioner is not performed even with the patrol prompting notification in step S13, that is, in a case where the state of the pump 2 has not been received from the pump 2 within a second predetermined time (for example, preferably about 15 minutes, which is about 1.5 times to twice the first predetermined time), the pump monitoring server 5 performs patrol prompting notification by escalation of gradually expanding a range of medical practitioner to be prompted to confirm the pump 2 (S15). A patrol prompting notification by escalation is issued by the nurse call system 7 toward a team of the medical practitioners having obligation of confirming the pump 2. In a case where none of the medical practitioners in this team has confirmed the pump 2, the pump monitoring server 5 further expands the range of the medical practitioner as a patrol prompting notification target. This configuration enables the medical practitioner to reliably confirm the pump 2.

Figure 3:
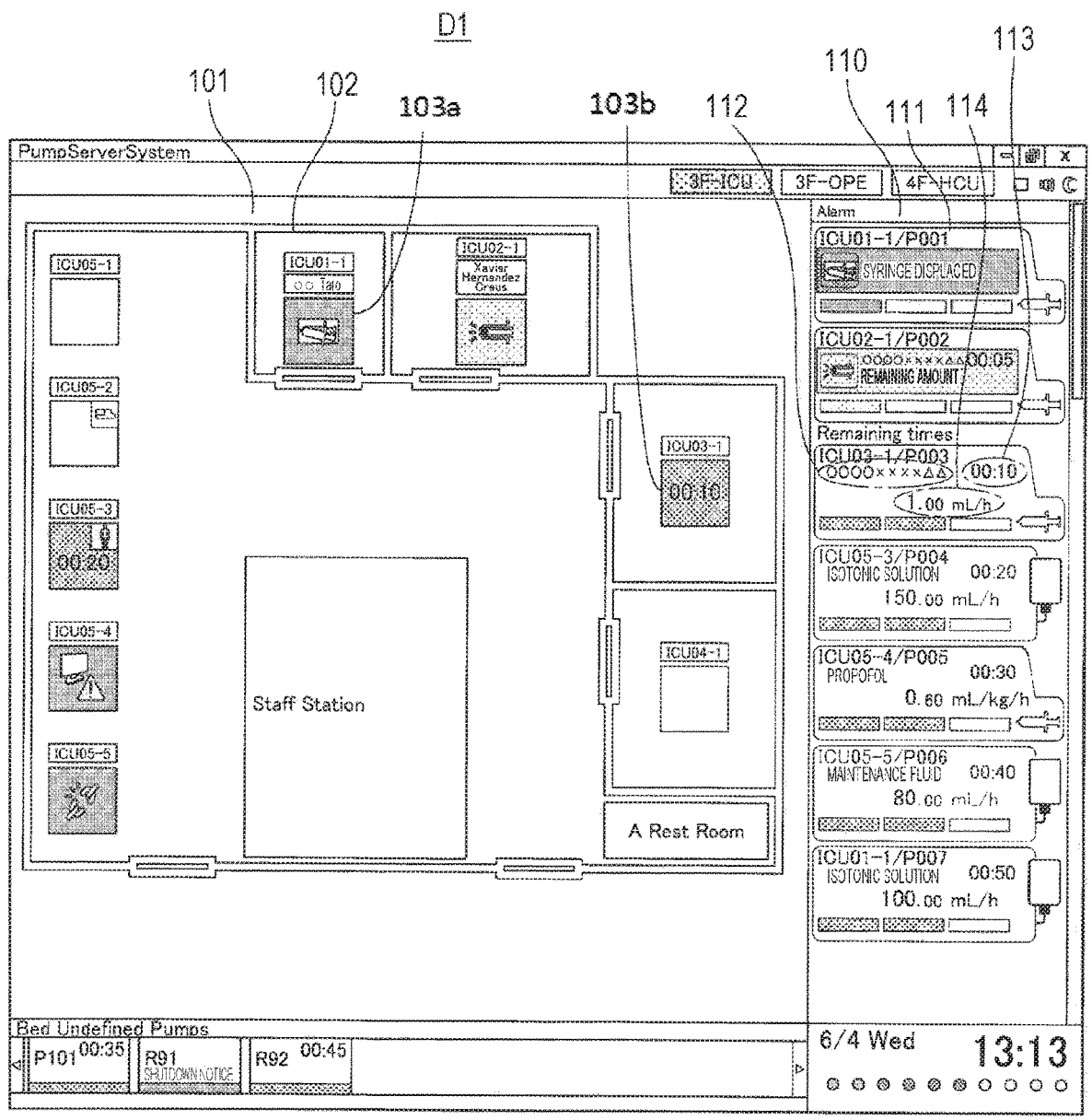
FIG. 3 is a screen configuration diagram illustrating an exemplary display of a central monitoring screen according to the embodiments presented herein.

FIG. 3 is a screen configuration diagram illustrating an exemplary display of a central monitoring screen D1.

The central monitoring screen D1 is displayed on the display unit 42 of the monitor terminal 4. The central monitoring screen D1 is formed with a hospital room layout 101 and a pump state display field 110.

The hospital room layout 101 illustrates arrangement of the hospital rooms identified by hospital room icons 102. The room icon 102 includes a state icon 103 indicating the name of the hospital room (for example, ICU 01-1), the name of the patient (for example, ○○ Taro), and the state of the pump 2 used in the corresponding hospital room. The state icon 103a indicates that abnormality of syringe displacement occurs in a hospital room with the hospital room name of ICU 01-1. Meanwhile, the state icon 103b of the hospital room with hospital room name of ICU 03-1 indicates medicine administration remaining time (for example, "00:10"). When a medical practitioner clicks on the room icon 102, it is also possible to display on the monitor terminal 4 an individual monitoring screen D2 (refer to FIG. 6 described below) corresponding to the clicked hospital room icon 102.

The pump state display field 110 lists a pump icon 111 indicating detailed states of the pumps 2 together with the state icons 103 of the pump 2 installed in individual hospital rooms. For example, the pump icon 111 with the hospital room name of ICU 01-1 indicates a state of "syringe displaced" together with the state icon 103a illustrated in the hospital room layout 101. Meanwhile, the pump icon 111 with the hospital room name of ICU 03-1 indicates a name of medicine 112 of the medicine delivered by the pump 2, administration remaining time 113b, and a flow rate 114. With this configuration, the medical practitioner can easily grasp the state of the pump 2 used in each of the hospital rooms merely by watching the central monitoring screen D1.

In the pump monitoring server 5 according to embodiments described above, in a case where confirmation of the pump 2 by the medical practitioner is not performed even after the first predetermined time has elapsed on the timer clocked by the clocking unit 54 clocking unit, the pump monitoring server 5 allows a message prompting the medical practitioner to confirm the pump 2 to be displayed on the user interface unit 23 and the monitor terminal 4 of the pump 2. With this configuration, the medical practitioner can rapidly confirm the pump 2, making it possible to prevent omission of confirmation of the pump 2.

Moreover, the fact that the medical practitioner has confirmed the pump 2 is recorded in the pump monitoring server 5 merely by the operation of pressing the confirmation button by the medical practitioner. This makes it possible to efficiently manage the state of the pump 2 uniformly with other medical practitioners.

Moreover, the pump monitoring server 5 prompts the medical practitioner to confirm the pump 2, and thereafter, in a case where confirmation of the pump 2 is not performed even after the second predetermined time has elapsed, the pump monitoring server 5 expands a prompting target of the pump 2 confirmation with escalation. This configuration enables the fact that the pump 2 has not been confirmed to be indicated to the team, or the like, of the medical practitioners having obligation of confirming the pump 2, making it possible to perform confirmation of the pump 2 more reliably and to reduce delay of the procedure.

Note that the confirmation button may be displayed on the touch panel of the user interface unit 23 of the pump 2. In this case, it is allowable to configure such that the medical practitioner confirms the pump 2, the pump control unit 22 transmits the state of the pump 2 to the pump monitoring server 5 by pressing the confirmation button displayed on the touch panel after the medical practitioner confirmed the pump 2.

Next, a configuration example and an operation example of a pump monitoring system 1A according to the embodiments presented herein will be described with reference to FIGS. 4 to 6.

Figure 4:
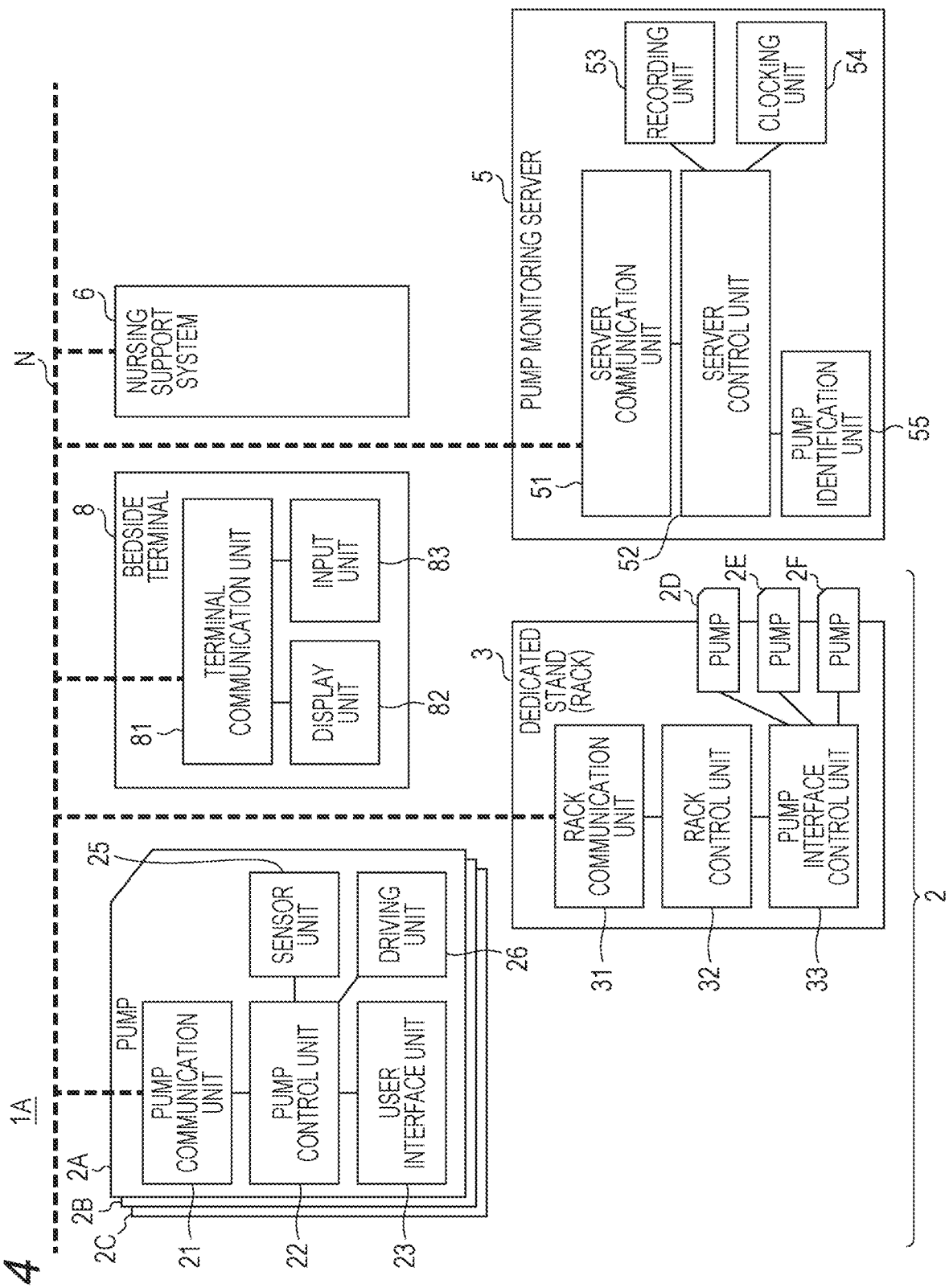
FIG. 4 is a block diagram illustrating an overall configuration example of a pump monitoring system according to embodiments presented herein.

FIG. 4 is a block diagram illustrating an overall configuration example of the pump monitoring system 1A.

The pump monitoring system 1A has a configuration similar to the above-described pump monitoring system 1 except that a bedside terminal 8 is provided instead of the monitor terminal 4, and the nurse call system 7 is removed.

Since the pump monitoring server 5 merely periodically monitors the presence or absence of confirmation of the pump 2, the pump 2 does not include the NFC reader unit 24 and the pump monitoring server 5 does not include the user identification unit 56. Accordingly, the pump control unit 22 can transmit solely the state of the pump 2 confirmed by the medical practitioner to the pump monitoring server 5. Moreover, the server control unit 52 records solely the state of the pump 2 received from the pump 2 in the recording unit 53 together with the time at which the state of the pump 2 is confirmed.

The bedside terminal 8 is installed in a hospital room where a patient is accommodated and is used as an exemplary display terminal. For example, it is installed at the side of the bed on which the patient is arranged or outside the hospital room. The bedside terminal 8 displays the layout of the pump 2 and the state of the pump 2 installed in the hospital room. Therefore, the medical practitioner can monitor the state of the pump 2 via the bedside terminal 8. The bedside terminal 8 includes a terminal communication unit 81, a display unit 82, and an input unit 83.

The terminal communication unit 81 is connected to the in-hospital network N and transmits the data received from the in-hospital network N to the display unit 82. Moreover, the data input from the input unit 83 is transmitted to the pump monitoring server 5 via the in-hospital network N.

The display unit 82 displays the data received from the terminal communication unit 81. For example, the display unit 82 includes a liquid crystal display and displays the individual monitoring screen D2 (refer to FIG. 6 described below).

The input unit 83 can input information on the pump 2 confirmed by the medical practitioner. In some cases, the display unit 82 and the input unit 83 are layered and used as a touch panel display.

<Exemplary Processing of Pump Monitoring System>

Figure 5:
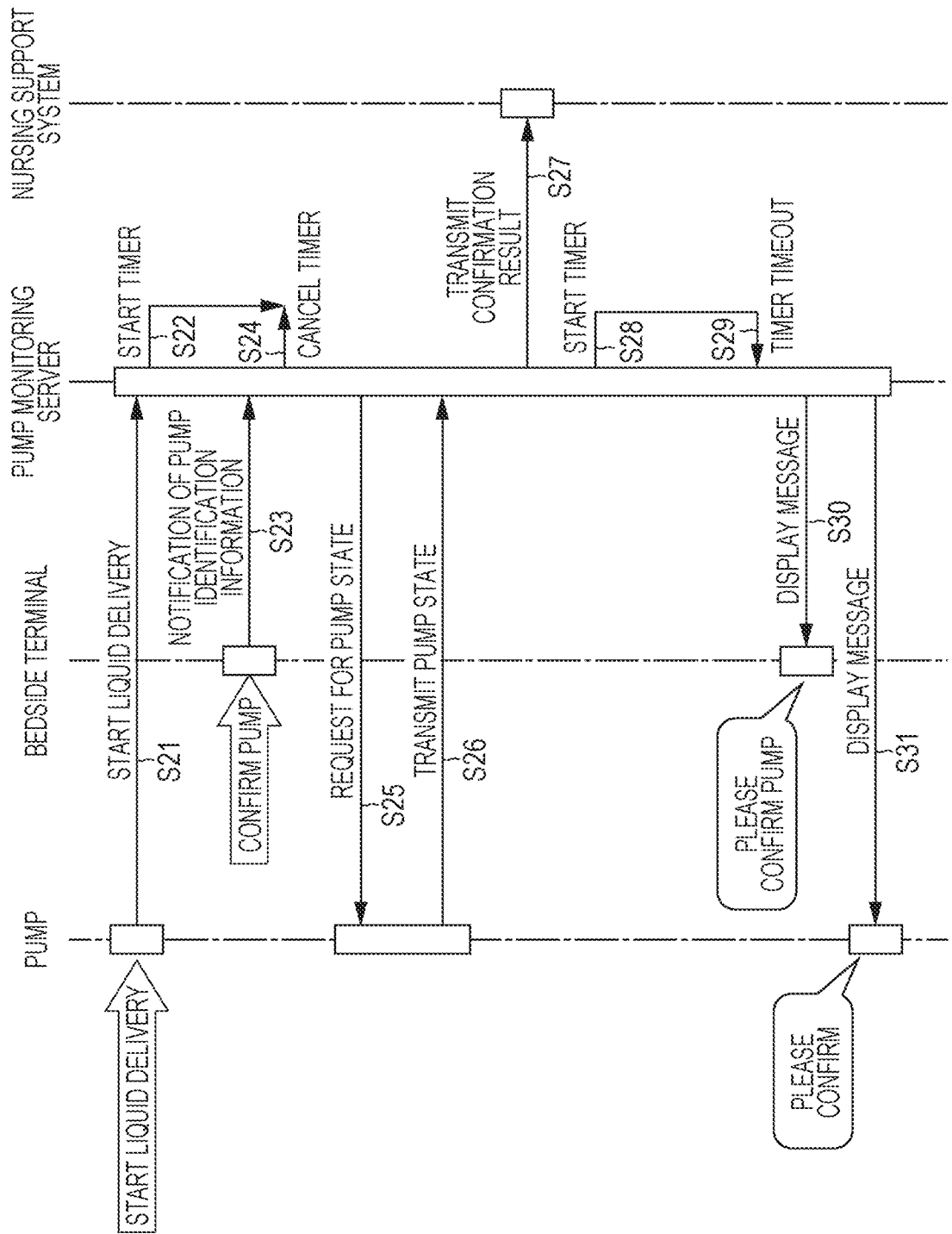
FIG. 5 is a sequence diagram illustrating exemplary processing of each of portions of the pump monitoring system according to the embodiments presented herein.

FIG. 5 is a sequence diagram illustrating exemplary processing of each of portions of the pump monitoring system 1A. Also in FIG. 5, the pump control unit 22 is substituted with the pump 2, and the server control unit 52 is substituted with the pump monitoring server 5.

First, processing at a normal condition will be described.

Upon starting delivery of medicine by the pump 2 (S21), the pump monitoring server 5 causes the clocking unit 54 to start clocking with the timer (S22). When a medical practitioner comes to the bedside terminal 8 and presses a confirmation button (pump icon 123 displayed on the individual monitoring screen D2 in FIG. 6 described below) indicating the pump 2 confirmed within the first predetermined time, the bedside terminal 8 notifies the pump monitoring server 5 of the pump identification information for identifying the confirmed pump and the user identification information of the medical practitioner (S23).

Upon receiving the pump identification information and the user identification information from the bedside terminal 8, the pump monitoring server 5 causes the clocking unit 54 to cancel (reset) the timer (S24). Subsequently, the pump monitoring server 5 requests the pump 2 to transmit the state of the pump 2 (S25).

The pump 2 transmits to the pump monitoring server 5 the state of the pump 2 at a time point when the pump 2 is confirmed by the medical practitioner (S26). Upon receiving the state of the pump 2, the pump monitoring server 5 records the state of the pump 2 in the recording unit 53 together with the time at which the state of the pump 2 is confirmed (for example, the time at which the state of the pump 2 is received). Then, the pump monitoring server 5 confirms whether the state of the pump 2 is normal or abnormal. Thereafter, the pump monitoring server 5 transmits the confirmation result of the state of the pump 2 to the nursing support system 6 (S27). The nursing support system 6 performs predetermined processing such as a nurse patrol notification in accordance with the confirmation result. While the pump 2 is delivering a liquid, the processing of steps S22 to S27 is repeated.

Next, processing at the occurrence of timeout of the timer will be described.

While the pump 2 is delivering liquid, the pump monitoring server 5 causes the clocking unit 54 to start clocking with the timer (S28). In a case where the pump monitoring server 5 has not received pump identification information of the pump 2 and the user identification information of the medical practitioner from the bedside terminal 8 within the first predetermined time, the pump monitoring server 5 cannot receive the confirmation information from the pump 2 and thus judges that the timeout of the timer occurred (S29). Subsequently, the pump monitoring server 5 allows an alarm message to be displayed on the bedside terminal 8 and the user interface unit 23 of the pump 2 (S30 and S31). An exemplary alarm message displayed on the bedside terminal 8 is "Please confirm the pump." An exemplary alarm message displayed on the user interface unit 23 of the pump 2 is "Please confirm".

Figure 6:
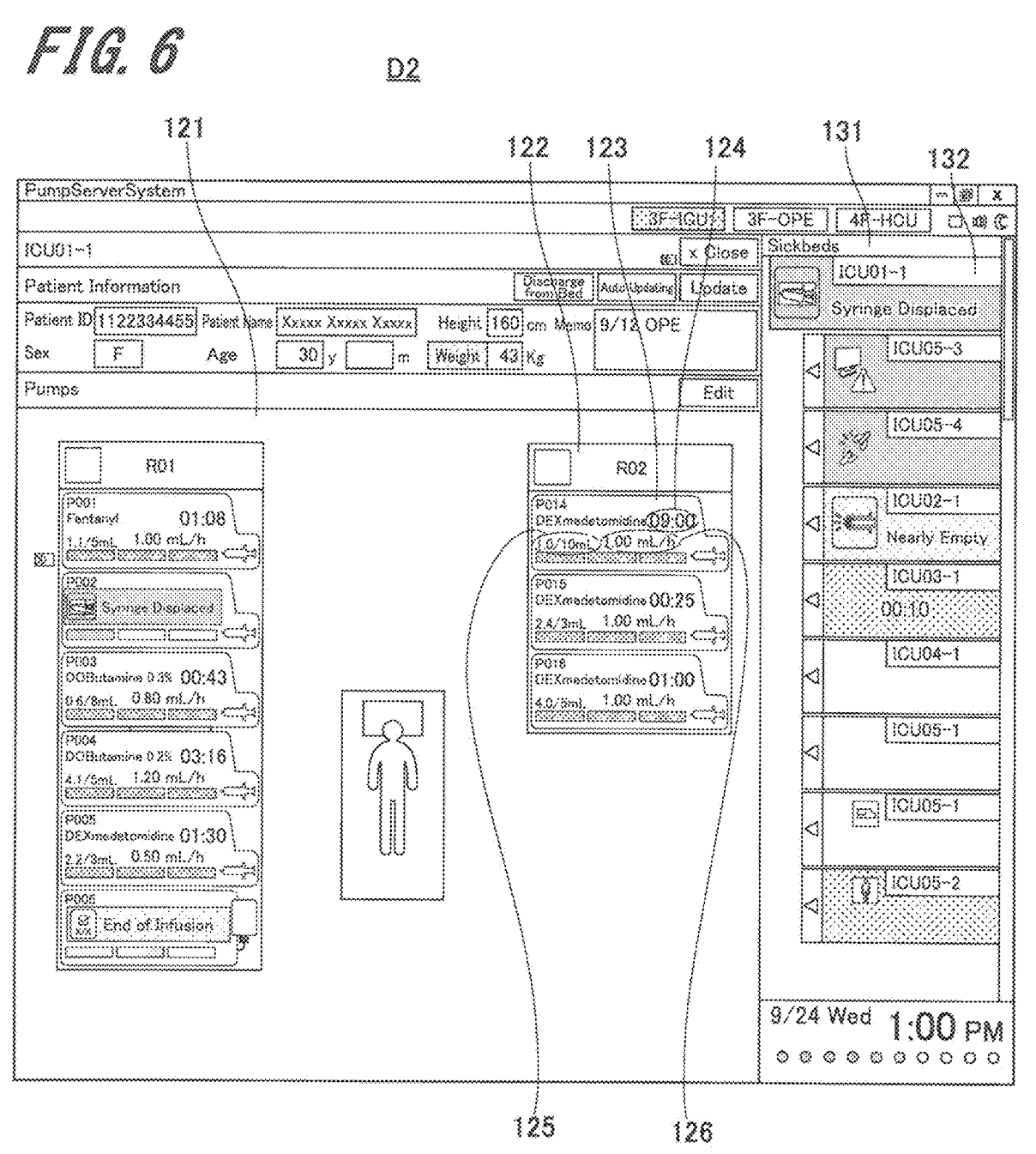

FIG. 6 is a screen configuration diagram illustrating an exemplary display of the individual monitoring screen D2.

The individual monitoring screen D2 is displayed on the display unit 82 of the bedside terminal 8. The individual monitoring screen D2 is formed with a pump layout 121 and a hospital room selection field 131.

The pump layout 121 indicates the arrangement of the pump 2 installed in the hospital room selected by the hospital room selection field 131. This example indicates by the rack icon 122 that the two dedicated stands 3 are installed in the hospital room. The rack icon 122 indicates a rack name (for example, R02). Furthermore, the rack icon 122 includes a pump icon 123 representing the pump 2 attached on the dedicated stand 3. Each of the pump icons 123 displays the identification information of the pump 2, the name of medicine, administration remaining time 124, administered amount or a scheduled administration amount 125, and a flow rate 126. When the pump icon 123 corresponding to the pump 2 confirmed by the medical practitioner is touched, the state of the pump 2 at the time point of touching is transmitted to the pump monitoring server 5 and recorded in the recording unit 53 of the pump monitoring server 5.

The hospital room selection field 131 displays a hospital room selection icon 132 together with the name of each of the hospital rooms. This example indicates the state of the pump 2 installed in the hospital room with the hospital room name of ICU 01-1. Note that by selecting a hospital room selection icon 132 other than the ICU 01-1, it is also possible to allow the state of the pump 2 installed in another room to be displayed at the pump layout 121.

According to the example of pump monitoring system 1A described above, the individual monitoring screen D2 is displayed on the bedside terminal 8. Accordingly, the bedside terminal 8 cannot be operated unless the medical practitioner comes to the hospital room. With this configuration, after confirming the pump 2, the medical practitioner touches the pump icon 123 displayed on the individual monitoring screen D2 displayed on the bedside terminal 8. Therefore, the pump monitoring server 5 can reliably grasp the time when the pump 2 is confirmed.

Note that the pump monitoring system 1A may include the nurse call system 7 and, in a case where no medical practitioner patrol is performed, it is allowable to perform notification by escalation similar to those as illustrated in steps S13 to S15 in FIG. 2.

Moreover, in the pump monitoring system 1 or 1A, the alarm issued by the pump monitoring server 5 may be an alarm for notifying a power supply abnormality, or the like, in the pump 2 in addition to notifying dislocation of the infusion tube or the syringe in the pump 2. With this configuration, the medical practitioner would be able to rapidly notice the abnormality occurring in the pump 2 and take a predetermined action.

Moreover, the information displayed on the portable terminal possessed by the medical practitioner may be a hospital room number, a code number associated with the alarm, or the like.

Moreover, while the NFC reader unit 24 provided in the pump 2 reads the user identification information of the medical practitioner, it is also allowable to provide a reading unit capable of reading biological information such as fingerprint authentication, vein authentication, pupil authentication as user identification information on the pump 2 or on the bedside terminal 8.

The embodiments presented herein are not limited to the above-described examples, but various other application examples and modifications are allowable within the scope and spirit of the present invention described in the appended claims.

For example, the above-described embodiments specify the details of the configuration of the apparatus and the system in order to clarify the embodiments presented herein and the embodiments presented herein are limited to those having all the configurations described above. It is possible to replace a portion of the configuration of one embodiment with the configuration of another embodiment, and it is possible to add a configuration of another embodiment to the configuration of an embodiment. Moreover, it is also possible to add, delete, and replace other configurations with respect to a portion of the configuration of each of the embodiments.

In addition, control lines and information lines indicate what is considered necessary for the explanation, and do not necessarily indicate all control lines and information lines in the product. In practice, it can be considered that substantially all the configurations are mutually connected.

What is claimed is:

1. A pump monitoring system comprising:
a pump configured to deliver a medicine to a patient, wherein the pump includes a pump control unit that transmits a state of the pump upon receiving a confirmation input provided by a medical practitioner; and
a pump monitoring server that receives the state of the pump transmitted by the pump control unit while the pump is delivering the medicine, and wherein the pump monitoring server includes:
a clocking unit that sets a timer clocking a liquid delivery time of the pump when the pump starts delivering the medicine; and
a server control unit that:
when the confirmation input is provided by the medical practitioner within a first predetermined time after the timer is set, records, in a recording unit, the state of the pump together with a time the medical practitioner provided the confirmation input, wherein the confirmation input verifies that the medical practitioner has confirmed the state of the pump while the pump is delivering the medicine; and
when the confirmation input is not provided by the medical practitioner within the first predetermined time after the timer is set, sends a message prompting the medical practitioner to confirm the state of the pump while the pump is delivering the medicine.

2. The pump monitoring system according to claim 1, wherein, when the confirmation input is not provided by the medical practitioner within a second predetermined time after the first predetermined time, the server control unit sends a second message prompting a team of medical practitioners to confirm the state of the pump while the pump is delivering the medicine.

3. The pump monitoring system according to claim 2, wherein the server control unit causes the clocking unit to automatically start the timer clocking the liquid delivery time after being notified of when the pump starts delivering the medicine, and, after the confirmation input is provided and the state of the pump is received from the pump control unit, the server control unit causes the clocking unit to reset the timer clocking a subsequent liquid delivery time of the pump.

4. The pump monitoring system according to claim 3, further comprising: a display terminal installed in an area where the team of medical practitioners gather, wherein the display terminal displays a layout of a hospital room accommodating the patient and the state of the pump installed in the hospital room.

5. The pump monitoring system according to claim 3, further comprising: a display terminal installed in a hospital room accommodating the patient, wherein the display terminal displays a layout of the pump installed in the hospital room and the state of the pump.

6. The pump monitoring system according to claim 5, wherein the pump includes a reading unit configured to read user identification information of the medical practitioner, wherein, when the confirmation input is provided by the medical practitioner, the pump control unit transmits the user identification information together with the state of the pump to the pump monitoring server, and in response the server control unit records, in the recording unit, the received user identification information together with the state of the pump.

7. The pump monitoring system according to claim 6, wherein the reading unit reads the user identification information from a storage medium storing the user identification information by wireless communication, and the pump includes a user interface unit for receiving the confirmation input from the medical practitioner proving that the medical practitioner has confirmed the state of the pump while the pump is delivering the medicine.

8. The pump monitoring system according to claim 7, further comprising: a rack to which a plurality of pumps including the pump is attached, wherein the rack includes a rack control unit configured to transmit to the pump monitoring server a state of each pump of the plurality of attached pumps and user identification information from each pump of the plurality of attached pumps.

9. A pump monitoring server in communication with a pump, the pump monitoring server comprising:
a clocking unit that sets a timer clocking a liquid delivery time of the pump when the pump starts delivering a medicine to a patient;
a recording unit; and
a server control unit in communication with the clocking unit and the recording unit, wherein the server control unit:
determines if a first period of time has elapsed since the timer clocking the liquid delivery time was set;
if the first period of time has not elapsed:
receives, from the pump, confirmation information in response to a medical practitioner providing a confirmation input, wherein the confirmation input verifies that the medical practitioner has confirmed a state of the pump at a first time while the pump is delivering the medicine; and
records, in the recording unit, the state of the pump and the first time;
if the first period of time has elapsed:
sends a first message prompting the medical practitioner to confirm the state of the pump while the pump is delivering the medicine.

10. The pump monitoring server according to claim 9, wherein, after expiration of the first period of time, the server control unit:
starts clocking a second period of time;
if the confirmation information of the state of the pump has not been received from the medical practitioner within the second period of time, sends a second message prompting a second medical practitioner to confirm the state of the pump while the pump is delivering the medicine.

11. The pump monitoring server according to claim 10, wherein the server control unit causes the clocking unit to automatically start the timer clocking the liquid delivery time after being notified of when the pump starts delivering the medicine, and, after the confirmation input is provided and the state of the pump is received from the pump, the server control unit causes the clocking unit to reset the timer clocking a subsequent liquid delivery time of the pump.

12. The pump monitoring server according to claim 11, wherein the server control unit sends the first message to a display terminal, wherein the display terminal displays a layout of a hospital room accommodating the patient and the state of the pump installed in the hospital room.

13. The pump monitoring server according to claim 12, wherein the display terminal is installed in a hospital room or a nurse's station.

14. The pump monitoring server according to claim 12, wherein the server control unit receives the state of the pump from a pump control unit of the pump, wherein the confirmation information comprises the state of the pump and a user identification information of the medical practitioner who provided the confirmation input confirming the state of the pump.

15. The pump monitoring server according to claim 14, wherein the pump control unit receives the user identification information from a reading unit associated with the pump, and wherein the pump control unit receives the confirmation input from a user interface associated with the pump.

16. The pump monitoring server according to claim 15, wherein the server control unit records, in the recording unit, the received user identification information together with the confirmation information of the state of the pump.

17. The pump monitoring server according to claim 16, wherein the reading unit reads, by wireless communication, the user identification information from a storage medium storing the user identification information.

18. The pump monitoring server according to claim 12, wherein the server control unit receives the state of the pump from a rack control unit associated with a rack, wherein the pump is attached to the rack with one or more other pumps.

19. A pump associated with a pump monitoring system comprising:
a user interface;
a reading unit; and
a pump control unit in communication with the user interface, the reading unit, and a pump monitoring server that monitors a state of the pump while the pump is delivering a liquid, wherein the pump control unit:
transmits a liquid delivery time of the pump to the pump monitoring server, the liquid delivery time defining a time when the pump starts delivering the liquid;
within a first predetermined time from the liquid delivery time:
receives, from a medical practitioner, a confirmation input from the user interface, the confirmation input verifying that the medical practitioner has confirmed the state of the pump while the pump is delivering the liquid;
receives a user identification information, of the medical practitioner who provided the confirmation input, from the reading unit;
transmits the state of the pump together with a time the medical practitioner provided the confirmation input confirming the state of the pump to the pump monitoring server, wherein the state of the pump comprises confirmation information associated with the confirmation input and the user identification information;
after the first predetermined time from the liquid delivery time:
receives, from the pump monitoring server, a first message prompting the medical practitioner to confirm the state of the pump while the pump is delivering the liquid; and
displays the first message on the user interface.

20. The pump according to claim 19, wherein the reading unit reads, by wireless communication, the user identification information from a storage medium storing the user identification information.

* * * * *